United States Patent
Lin et al.

(10) Patent No.: US 9,884,207 B2
(45) Date of Patent: Feb. 6, 2018

(54) DETECTOR FOR MEASURING SCANNING ION BEAMS IN RADIATION THERAPY

(71) Applicants: ACADEMIA SINICA, Taipei (TW); National Central University, Taoyuan (TW)

(72) Inventors: Chih-Hsun Lin, Taipei (TW); Ping-Kun Teng, New Taipei (TW); Augustine Ei-Fong Chen, Taoyuan (TW)

(73) Assignees: Academia Sinica, Taipei (TW); National Central University, Taoyuan (*) Notice: Subject to any disclaimer, the term of this patent is extended or adjusted under 35 U.S.C. 154(b) by 0 days.

(21) Appl. No.: 15/432,432

(22) Filed: Feb. 14, 2017

(65) Prior Publication Data
US 2017/0266464 A1    Sep. 21, 2017

Related U.S. Application Data

(60) Provisional application No. 62/310,462, filed on Mar. 18, 2016.

(51) Int. Cl.
*A61N 5/10*    (2006.01)

(52) U.S. Cl.
CPC ......... *A61N 5/1048* (2013.01); *A61N 5/1077* (2013.01)

(58) Field of Classification Search
CPC .................................................. A61N 5/1048
See application file for complete search history.

(56) References Cited

U.S. PATENT DOCUMENTS

| 2015/0031933 A1 | 1/2015 | Yamamoto et al. |
| 2016/0250500 A1* | 9/2016 | Boisseau ............. A61N 5/1048 |
| | | 250/370.01 |
| 2017/0003403 A1* | 1/2017 | Menichelli ........... A61N 5/1075 |

* cited by examiner

*Primary Examiner* — David Porta
*Assistant Examiner* — Hugh H Maupin
(74) *Attorney, Agent, or Firm* — Muncy, Geissler, Olds & Lowe, P.C.

(57) ABSTRACT

A detector for measuring scanning ion beams in radiation therapy sequentially includes a first high voltage electrode, a first spacing member, and a segmented electrode. The first spacing member is connected to the first high voltage electrode and the segmented electrode to form a first ionization cavity. The first ionization cavity is formed with a plurality of first reading electrodes and a plurality of second reading electrodes therein. A second spacing member and a second high voltage electrode are further sequentially disposed. The second spacing member is connected to the second high voltage electrode and the segmented electrode to form a second ionization cavity. The first reading electrodes and the second reading electrodes are respectively formed in the first ionization cavity and the second ionization cavity. With the first reading electrodes and the second reading electrodes in different directions, highly accurate space resolution, space dosage and scanning speed are achieved.

13 Claims, 11 Drawing Sheets

DETECTOR FOR MEASURING SCANNING ION BEAMS IN RADIATION THERAPY

FIELD OF THE INVENTION

The present invention relates to a detector, and particularly to a detector for measuring scanning ion beams in radiation therapy.

BACKGROUND OF THE INVENTION

Cancer, also referred to as malignant tumors, is a result of abnormally proliferated cells that further invade other parts of a human body, and is one main cause for human deaths. Cancer can be treated by surgery, chemotherapy, radiation therapy, immunotherapy, monoclonal antibody therapy or other therapies. Among the above treatments, radiation therapy frequently serves as a most direct or auxiliary method for treating cancer. By killing cancer cells, reducing tumors and damaging genetic substances of cells with radiation, radiation therapy prohibits cell growth or dividing to further control the growth of cancer cells.

For example, the U.S. Patent Publication No. 20150031933, "Range Shifter and Particle Radiotherapy Device", discloses a common radiotherapy device. The particle therapy device includes an accelerator that generates a particle beam, a plurality of treatment rooms, a plurality of irradiation devices, and a plurality of range shifters disposed in the irradiation devices. The particle beam enters the treatment rooms from the accelerator. The irradiation devices are respectively disposed in the treatment rooms, and irradiate the particle beam onto an irradiation area of an irradiation target. Each range shifter includes a transmissive plate and a holding portion that holds the transmissive plate. By adjusting the thickness of the transmissive plate, the particle beam may be given with different attenuation amounts, such that the energy of the particle beam can be adjusted.

In general use, a detector is also used in conjunction to confirm the accuracy of parameters of the particle beam and the amount of radiation transmitted. In a conventional treatment, a large-area radiation exposure is applied, and a range of radiation is limited using a predetermined shield manufactured according to a size of tumors. Thus, the measurement of a specific position is usually performed by a two-dimensional detector or a small-size detector (single-channel). In a new ion treatment, the position of tumors is scanned using small-size ion beams at a scanning speed of 20 m/sec, and the dosage can be controlled by controlling the scanning speed. However, due to an excessively large space resolution and an inadequate measuring speed, a conventional detector is incapable of accurately measuring such scanning ion beams. Therefore, there is a need for a solution that is capable of increasing the space resolution and measuring speed to accurately measure the parameters and radiation dosage.

SUMMARY OF THE INVENTION

It is a primary object of the present invention to solve issues of the prior art. In the prior art, due to an excessively space resolution and an inadequate measuring speed, a conventional detector is incapable of accurately measuring scanning ion beams.

To achieve the above object, the present invention provides a detector for measuring scanning ion beams in radiation therapy. The detector includes a first high voltage electrode, a second high voltage electrode, a dual-sided segmented electrode disposed between the first high voltage electrode and the second high voltage electrode, a first spacing member disposed between the first high voltage electrode and the dual-sided segmented electrode, and a second spacing member disposed between the second high voltage electrode and the dual-sided segmented electrode. The first high voltage electrode includes a first high voltage region, and a first grounded region surrounding the first high voltage region. The second high voltage electrode includes a second high voltage region, and a second grounded region surrounding the second high voltage region. The dual-sided segmented electrode includes a first detection region disposed correspondingly to the first high voltage region, a second detection region having a rear side facing the first detection region and disposed correspondingly to the second high voltage region, a third grounded region surrounding the first detection region and the second detection region, a first reading electrode disposed in the first detection region, and a second reading electrode disposed in the second detection region. The first spacing member includes a first frame body connected to the first grounded region and the third grounded region, and a first ionization cavity formed by the first frame body surrounding the first high voltage region and the first detection region. The first reading electrode is accommodated in the first ionization cavity. The second spacing member includes a second frame body connected to the second grounded region and the third grounded region, and a second ionization cavity formed by the second frame body surrounding the second high voltage region and the second detection region. The second reading electrode is accommodated in the second ionization cavity.

To achieve the above object, the present invention provides a detector for measuring scanning ion beams in radiation therapy. The detector includes a first high voltage electrode, a segmented electrode assembly, and a first spacing member disposed between the first high voltage electrode and the segmented electrode assembly. The first high voltage electrode includes a first high voltage region, and a first grounded region surrounding the first high voltage region. The segmented electrode assembly includes a segmented electrode, a substrate carrying the segmented electrode, and an inner connecting line. The segmented electrode includes a plurality of reading electrodes and a plurality of second reading electrodes. The first reading electrodes and the second reading electrodes extend along different directions, respectively. The substrate includes an upper substrate, a lower substrate and an intermediate layer disposed between the upper substrate and the lower substrate. The upper substrate includes an upper surface, a plurality of first through holes penetrating the upper surface and being in communication with the first reading electrodes, and a plurality of second through holes penetrating the upper surface and being in communication with the second reading electrodes. The upper surface includes a first detection region disposed correspondingly to the first high voltage region, and a third grounded region surrounding the first detection region. The inner connecting line includes a plurality of first conductive sections disposed at the first through holes and electrically connected to the first reading electrodes, a plurality of first conductive wires disposed on the lower substrate and electrically connected to the first conductive sections, a plurality of second conductive sections disposed at the second through holes and electrically connected to the second reading electrodes, and a plurality of second conductive wires disposed on the intermediate layer and electrically connected to the second conductive sections. The first spacing member includes a first frame body connected to the first grounded region and the third grounded region, and a first ionization cavity formed by the first frame body surrounding the first high voltage region and the first detection region.

In conclusion, by disposing the first ionization cavity and the second ionization cavity respectively collaborating with the first reading electrode and the second reading electrode disposed, or by disposing one ionization cavity with the first reading electrodes and the second reading electrodes formed therein, the present invention enhances the space resolution and increases the measuring speed, thereby achieving highly accurate space resolution, space dosage and scanning speed.

DETAILED DESCRIPTION OF THE PREFERRED EMBODIMENTS

Figure 1A:
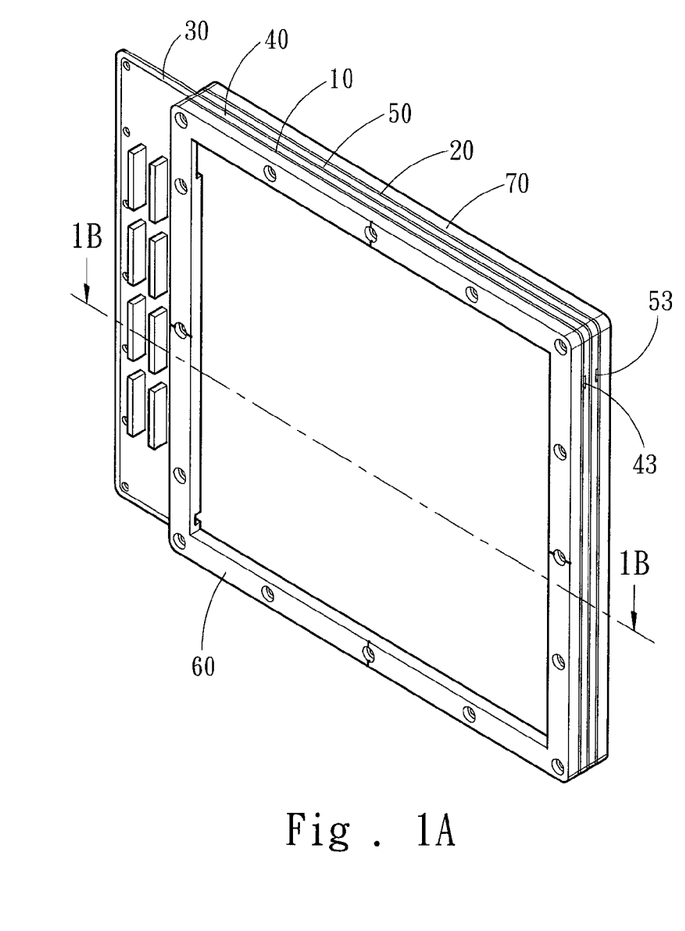
FIG. 1A is a perspective structural diagram according to a first embodiment of the present invention.
Figure 1B:
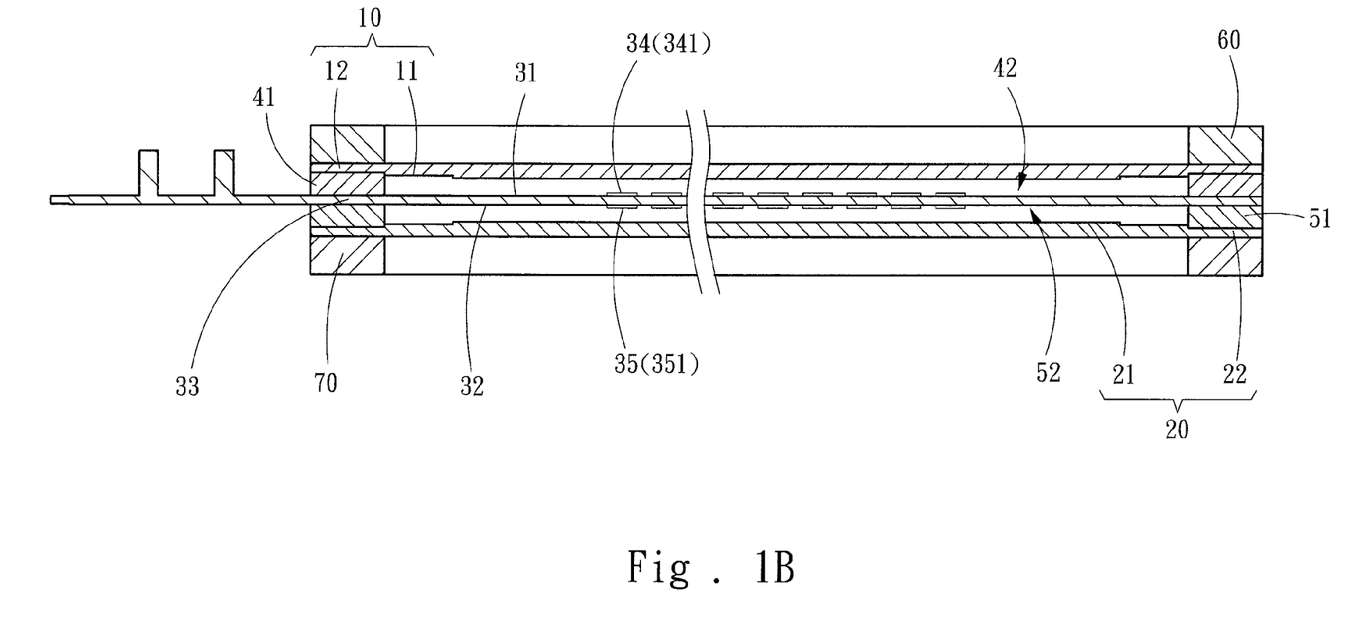
FIG. 1B is a cross-section structural diagram of FIG. 1A along 1B-1B of the present invention.
Figure 2:
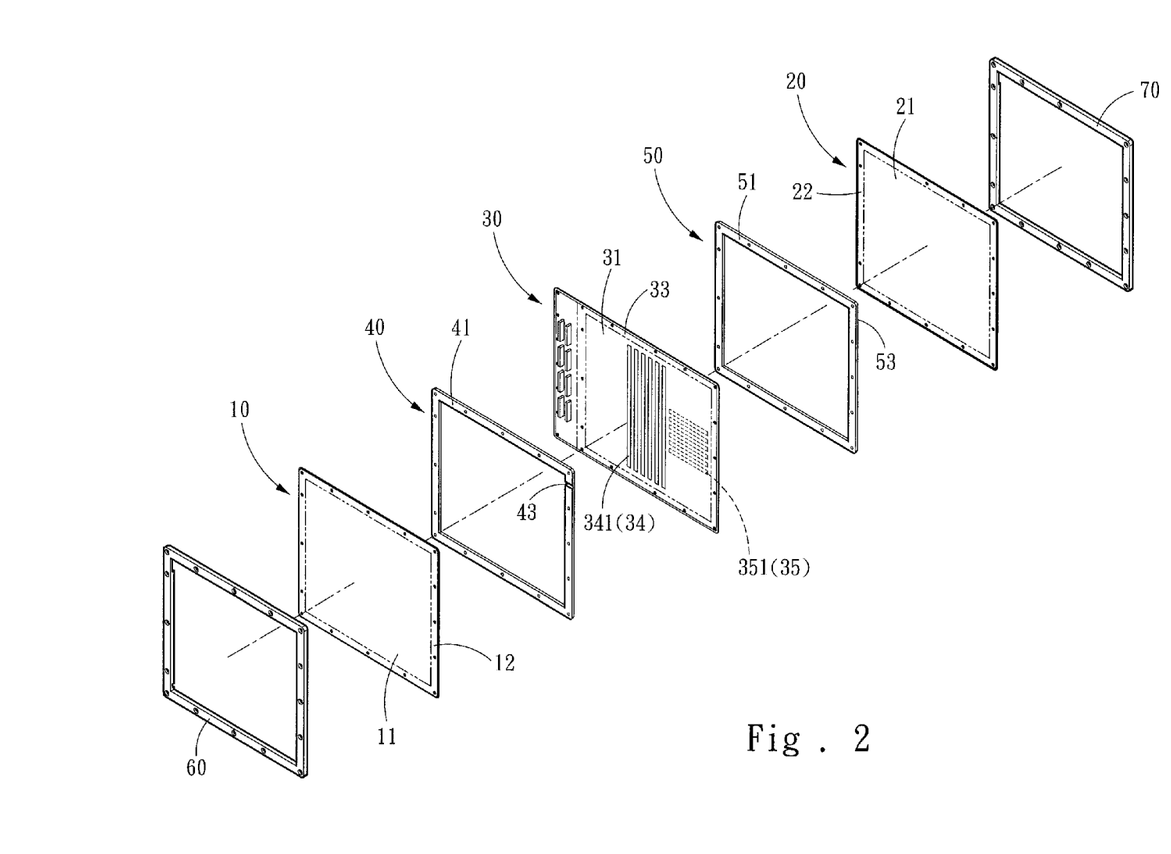
FIG. 2 is an exploded structural diagram according to the first embodiment of the present invention.

FIG. 1A, FIG. 1B and FIG. 2 are a perspective structural diagram, a cross-section structural diagram of FIG. 1A along 1B-1B and an exploded structural diagram according to a first embodiment of the present invention. The present invention provides a detector for measuring scanning ion beams in radiation therapy. Referring to FIG. 1A, FIG. 1B and FIG. 2, the detector of the present invention includes a first high voltage electrode 10, a first spacing member 40, a dual-side segmented electrode 30, a second spacing member 50 and a second high voltage electrode 20. The first high voltage electrode 10 includes a first high voltage region 11, and a first grounded region 12 surrounding the first high voltage region 11. The second high voltage electrode 20 includes a second high voltage region 21, and a second grounded region 22 surrounding the second high voltage region 21. The dual-sided segmented electrode 30, disposed between the first high voltage electrode 10 and the second high voltage electrode 20, includes a first detection region 31 disposed correspondingly to the first high voltage region 11, a second detection region 32 having a rear side facing the first detection region 31 and disposed correspondingly to the second high voltage region 21, a third grounded region 33 surrounding the first detection region 31 and the second detection region 32, a first reading electrode 34 disposed in the first detection region 31, and a second reading electrode 35 disposed in the second detection region 32. The first spacing member 40, disposed between the first high voltage electrode 10 and the dual-sided segmented electrode 30, includes a first frame body 41 connected to the first grounded region 12 and the third grounded region 33, and a first ionization cavity 42 formed by the first frame body 41 surrounding the first high voltage region 11 and the first detection region 31. The first reading electrode 34 is accommodated in the first ionization cavity 42. The second spacing member 50, disposed between the second high voltage electrode 20 and the dual-sided segmented electrode 30, includes a second frame body 51 connected to the second grounded region 22 and the third grounded region 33, and a second ionization cavity 52 formed by the second frame body 51 surrounding the second high voltage region 21 and the second detection region 32. The second reading electrode 35 is accommodated in the second ionization cavity 52.

As the present invention includes the first ionization cavity 42 and the second ionization cavity 52, the present invention may be used for measuring particle beams in the X and Y directions. In the embodiment, the first reading electrode 34 includes a plurality of longitudinal electrodes 341, and the second reading electrode 35 includes a plurality of lateral electrodes 351. The longitudinal electrodes 341 and the lateral electrodes 351 are respectively in a quantity of 127, and are spaced from one another by 2 mm. As such, with a space position resolution smaller than 0.2 mm for the shape measurement of ion beams, the present invention is capable of accurately measuring the position and track of a particle beam. Further, the measuring speed of the present invention may be as high as 10 kHz. Therefore, time variations in parameters of particle beams or radiation dosage can be precisely determined to enhance the measurement accuracy.

The first spacing member 40 further includes a first ventilation portion 43 disposed at the first frame body 41, and the second spacing member 50 further includes a second ventilation portion 53 disposed at the second frame body 51. The first ventilation portion 43 allows the first ionization cavity 42 to be in communication with the exterior, and the second ventilation portion 53 allows the second ionization cavity 52 to be in communication with the exterior. Thus, air from the exterior may enter the first ionization cavity 42 and the second ionization cavity 52 via the first ventilation portion 43 and the second ventilation portion 53, respectively. In the embodiment, the first spacing member 40 and the second spacing member 50 are respectively in a quantity of one, and are mutually symmetrically arranged. It should be noted that the above quantity and arrangement of the first spacing member 40 and the second spacing member 50 are an example, and are not to be construed as a limitation to the present invention. For example, the thickness of the first spacing member 40 and the second spacing member 50 may be 3 mm, and may be adjusted according to user requirements.

To securely join the first high voltage electrode 10, the first spacing member 40, the dual-sided segmented electrode 30, the second spacing member 50 and the second high voltage electrode 20, a first fastening member 60 may be disposed at one side of the first high voltage electrode 10 away from the dual-sided segmented electrode 30, and a second fastening member 70 may be disposed at one side of the second high voltage electrode 20 away from the dual-sided segmented electrode 30. In the embodiment, for example but not limited to, the first fastening member 60 and the second fastening member 70 may be securely joined by a locking fastening means.

In an application process of the present invention, a voltage difference is applied to the dual-sided segmented electrode 30, the first high voltage electrode 10 and the second high voltage electrode 20 to form an electric field. A particle beam to be tested enters the first ionization cavity 42 (the X direction) and the second ionization cavity 52 (the Y direction), such that the air in the first ionization cavity 42 and the second ionization cavity 52 is ionized. With the effect of the electric field, the ions are gathered on the first detection region 31 and the second detection region 32 of the dual-sided segmented electrode 30. The first reading electrode 34 and the second reading electrode 35 then collect the ions gathered on the first detection region 31 and the second detection region 32 for subsequent analysis.

FIG. 3A to FIG. 7C show a second embodiment of the present invention. Referring to FIG. 3A to FIG. 7C, in the embodiment, a detector for measuring scanning ion beams in radiation therapy includes a first high voltage electrode 10, a segmented electrode assembly 80, and a first spacing member 40 disposed between the first high voltage electrode 10 and the segmented electrode assembly 80. The first high voltage electrode 10 includes a first high voltage region 11, and a first grounded region 12 surrounding the first high voltage region 11. The segmented electrode assembly 80 is disposed at one side of the first high voltage electrode 10, and includes a segmented electrode 82, a substrate carrying the segmented electrode 82, and an inner connecting line 84. The segmented electrode 82 includes a plurality of first reading electrodes 821 and a plurality of second reading electrodes 822. The first reading electrodes 821 and the second reading electrodes 822 extend along different directions, respectively. The substrate includes an upper substrate 85, a lower substrate 81, and an intermediate layer 83 disposed between the upper substrate 85 and the lower substrate 81.

The upper substrate 85 includes an upper surface 86, a plurality of first through holes 87 penetrating the upper surface 86 and being in communication with the first reading electrodes 821, and a plurality of second through holes 88 penetrating the upper surface 86 and being in communication with the second reading electrodes 822. The upper surface 86 includes a first detection region 861 disposed correspondingly to the first high voltage region 11, and a third grounded region 862 surrounding the first detection region 861. The inner connecting line 84 includes a plurality of first conductive sections 841 disposed at the first through holes 87 and electrically connected to the first reading electrodes 821, a plurality of first conductive wires 842 disposed on the lower substrate 81 and electrically connected to the first conductive sections 841, a plurality of second conductive sections 843 disposed at the second through holes 88 and electrically connected to the second reading electrodes 822, and a plurality of second conductive wires 844 disposed on the intermediate layer 83 and electrically connected to the second conductive sections 843.

Figure 3A:
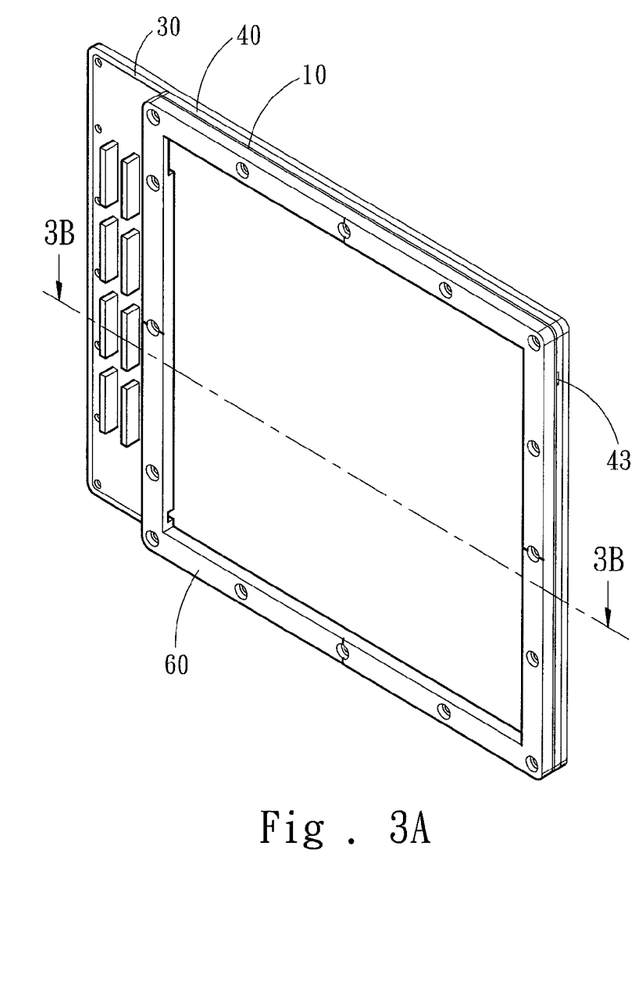
FIG. 3A is a perspective structural diagram according to a second embodiment of the present invention.
Figure 3B:
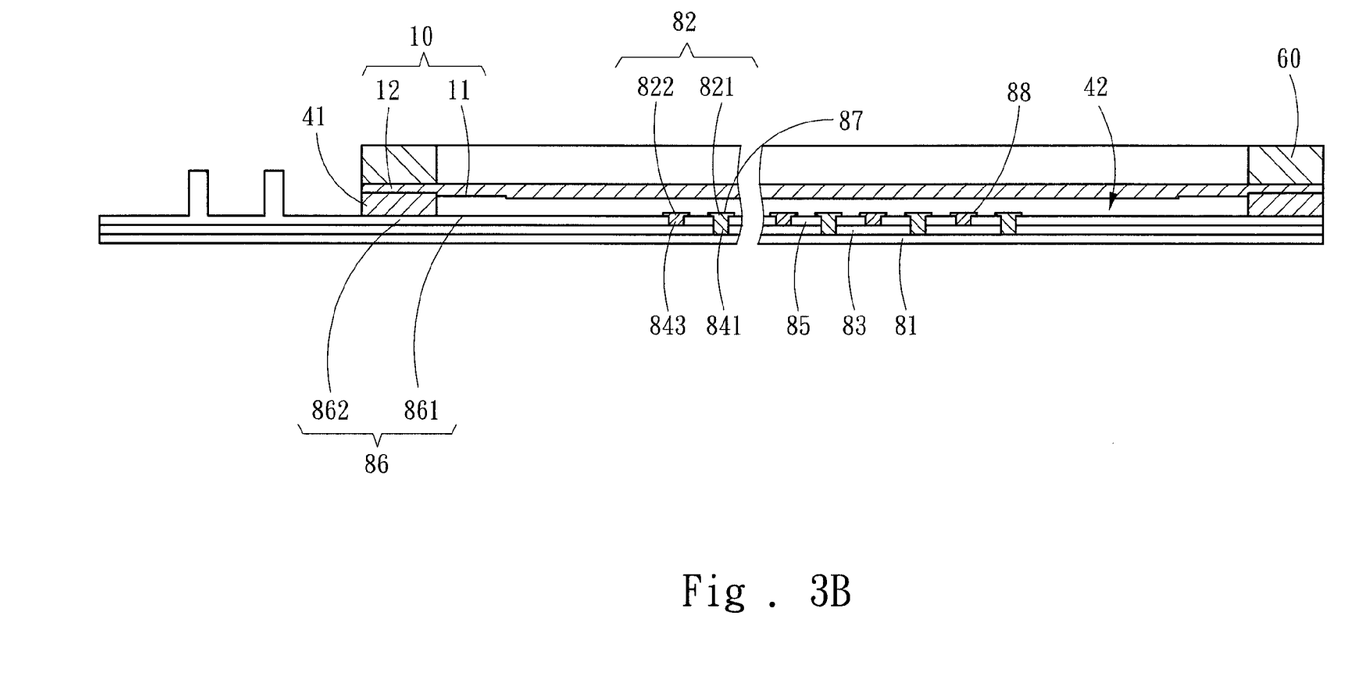
FIG. 3B is a partial cross-section structural diagram according to the second embodiment of the present invention.
Figure 4:
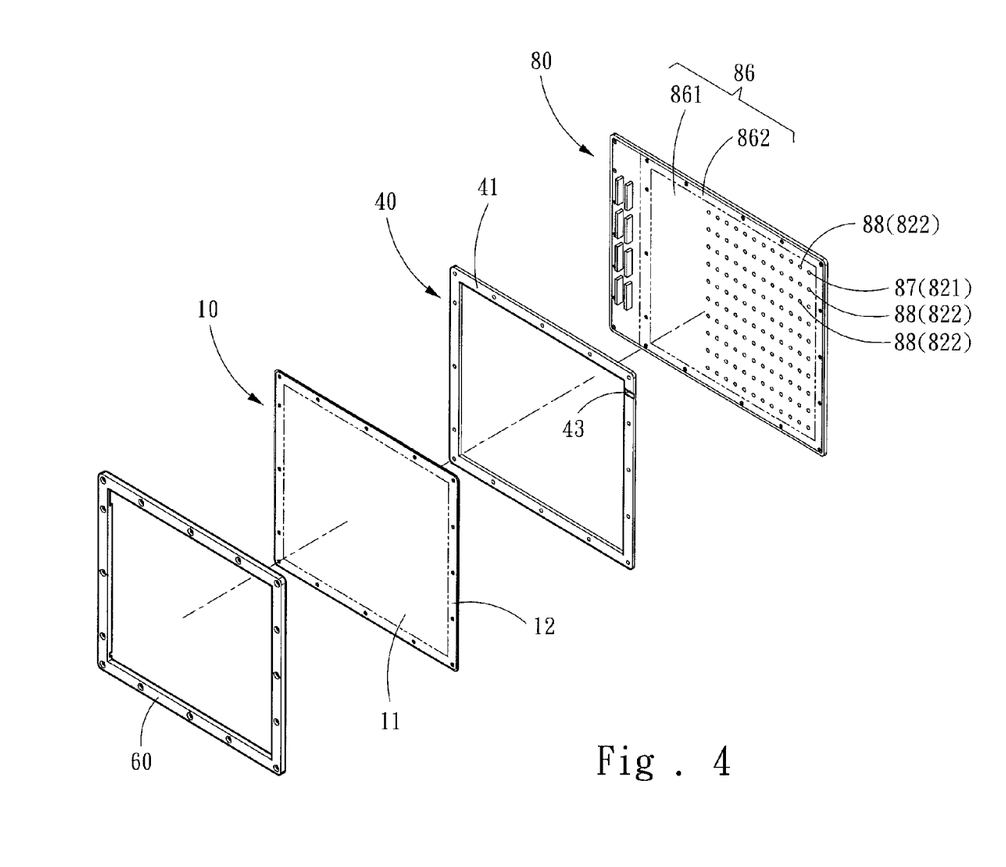
FIG. 4 is an exploded structural diagram according to the second embodiment of the present invention.

The first spacing member 40 includes a first frame body 41 connected to the first grounded region 12 and the third grounded region 862, and a first ionization cavity 42 formed by the first frame body 41 surrounding the first high voltage region 11 and the first detection region 861.

Figure 5:
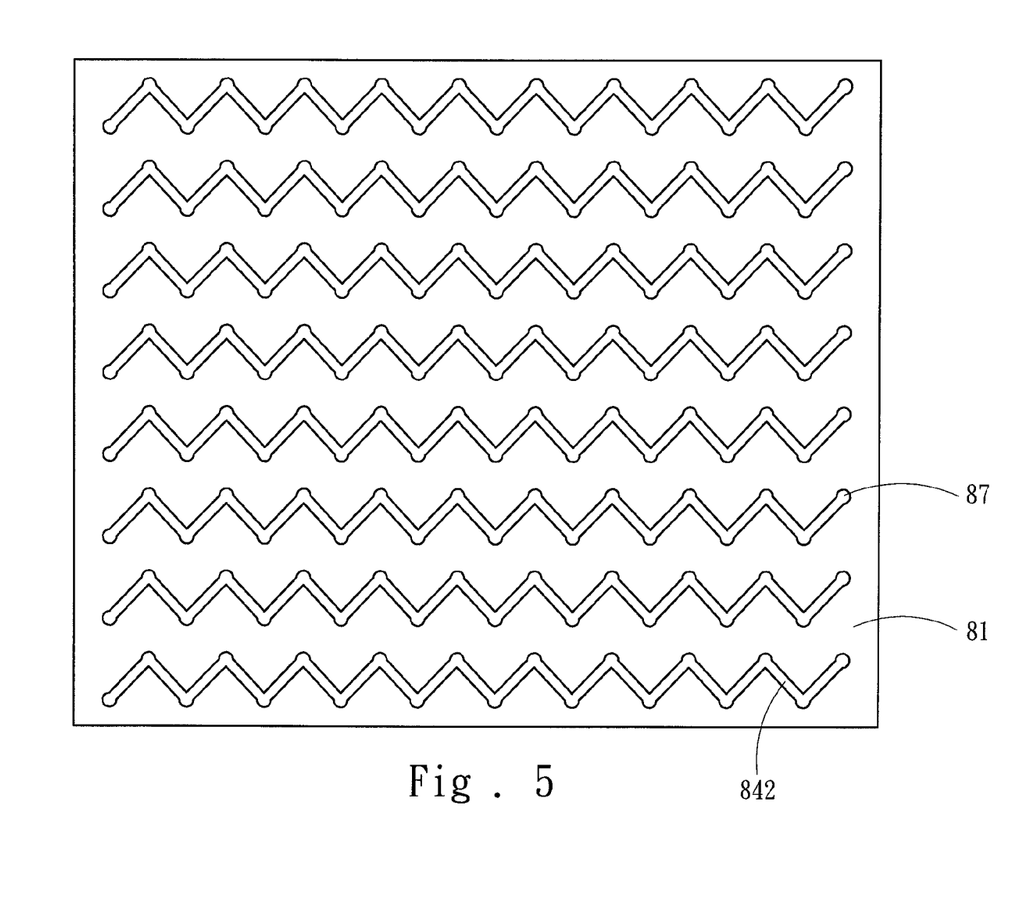
FIG. 5 is a first schematic diagram of an inner layer of a segmented electrode according to the second embodiment of the present invention.
Figure 6:
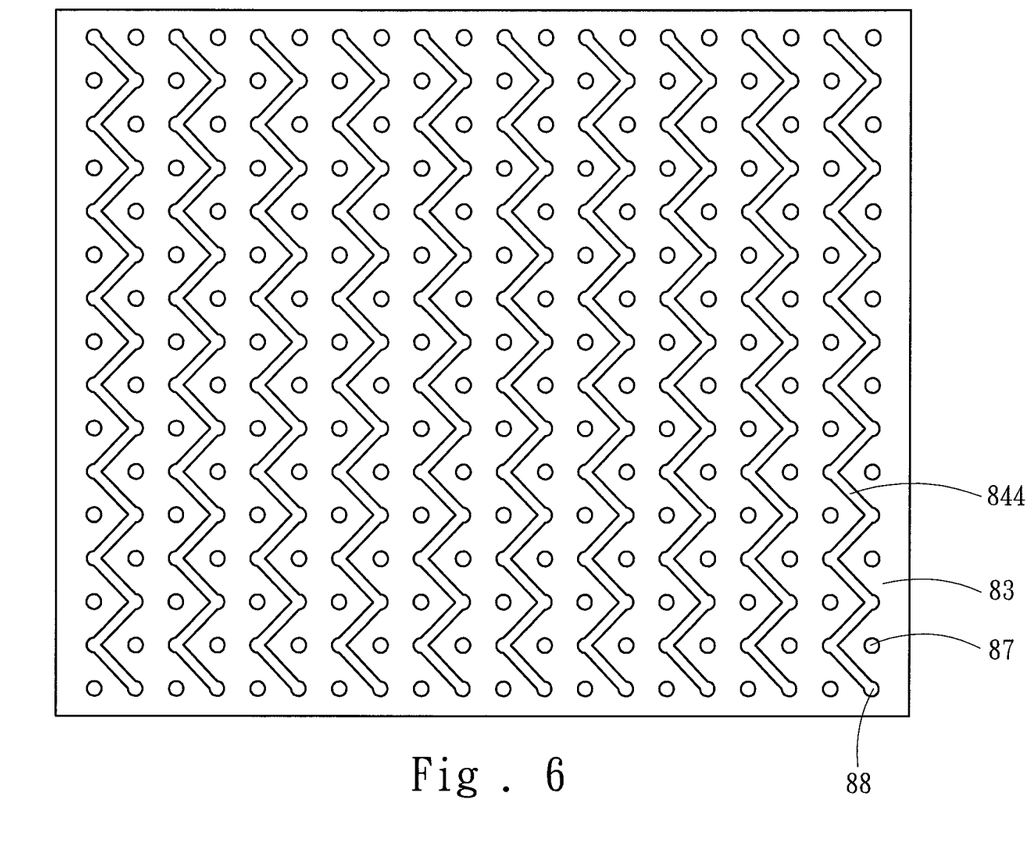
FIG. 6 is a second schematic diagram of an inner layer of a segmented electrode according to the second embodiment of the present invention.

Referring to FIG. 5 and FIG. 6 showing schematic diagrams of inner layers of a segmented electrode assembly 80 according to the embodiment, it is seen that the first conductive wires 842 are disposed in parallel to one another on the lower substrate 81, and the second conductive wires 844 are disposed in parallel to one another on the intermediate layer 83.

Figure 7A:
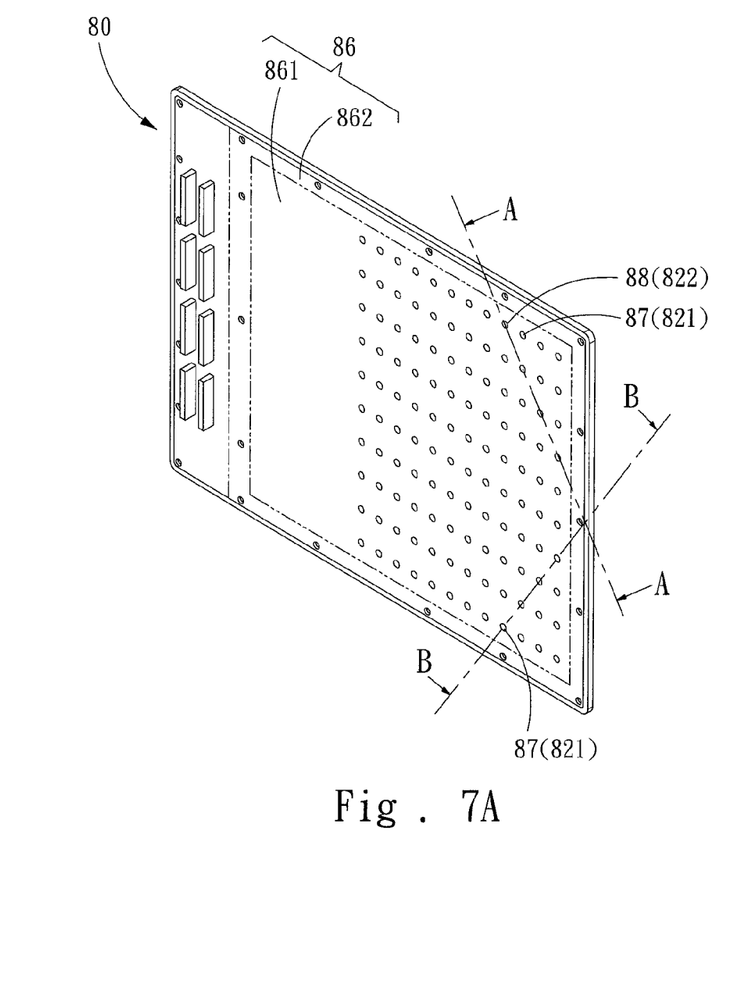
FIG. 7A is a perspective structural diagram of a segmented electrode according to the second embodiment of the present invention.
Figure 7B:
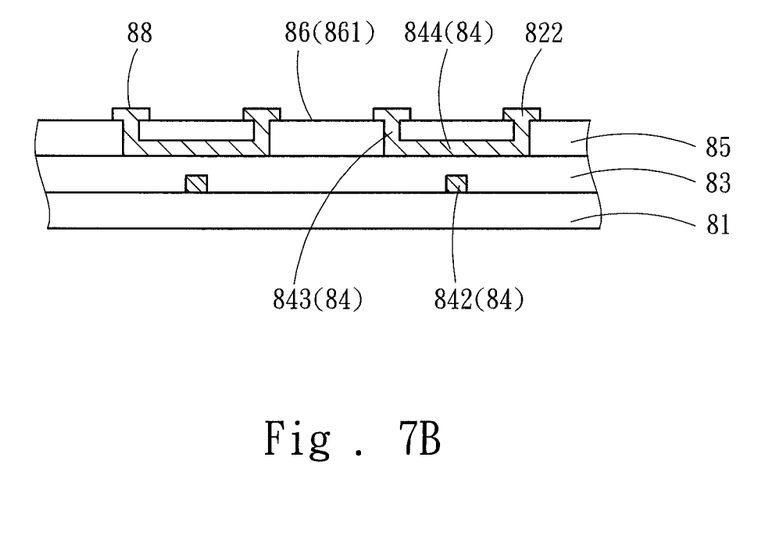
FIG. 7B is a cross-section structural diagram of FIG. 7A along A-A of the present invention.
Figure 7C:
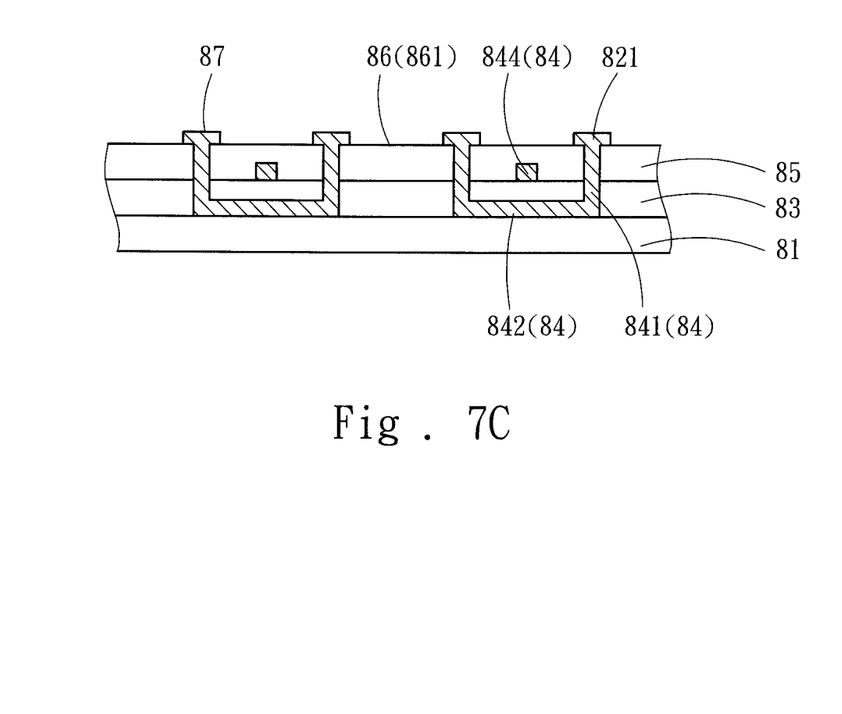
FIG. 7C is a cross-section structural diagram of FIG. 7A along B-B of the present invention.

Referring to FIG. 7A to FIG. 7C, the first reading electrodes 821 and the second reading electrodes 822 are formed at the first detection region 861, and are located in the first ionization cavity 42. Further, the first conductive sections 841 have two ends thereof respectively connected to the first reading electrodes 821 and the first conductive wires 842, and the second conductive sections 843 have two ends thereof respectively connected to the second reading electrodes 822 and the second conductive wires 844. In the embodiment, the first reading electrodes 821 are spaced by 2 mm from one another, and the second reading electrodes 822 are also spaced by 2 mm from one another. Thus, this embodiments also achieves a space position resolution smaller than 2 mm and a measuring speed greater than 10 kHz.

Further, this embodiment similarly includes a first ventilation portion 43 disposed at the first frame body 41, and a first fastening member 60 disposed at one side of the first high voltage electrode 10 away from the segmented electrode assembly 80. The first ventilation portion 43 allows the first ionization cavity 42 to be in communication with the exterior via the first ventilation portion 43, and the first fastening member 60 securely joins the first high voltage electrode 10, the segmented electrode assembly 80 and the first spacing member 40.

Regarding operations of the embodiment, a high voltage is first applied to the segmented electrode assembly 80 at the first high voltage electrode 10 to form an electric field. When a particle beam to be measured penetrates the first high voltage region 11 and enters the first ionization cavity 42, the particle beam ionizes air in the first ionization cavity 42. With the effect of the electric field, the ions are gathered on the first detection region 861 of the segmented electrode assembly 80. The first conductive sections 841 and the second conductive sections 843 revealed at the first detection region 861 then collect the ions gathered on the first detection region 861 for subsequent analysis.

In conclusion, in the present invention, by disposing the first ionization cavity and the second ionization cavity in conjunction with the dual-sided longitudinal and lateral electrodes, or by disposing one ionization cavity with the first reading electrodes and the second reading electrodes formed therein, the present invention enhances the space resolution and increases the measuring speed, thereby achieving highly accurate space resolution, space dosage and scanning speed.

What is claimed is:

1. A detector for measuring scanning ion beams in radiation therapy, comprising:
a first high voltage electrode, comprising a first high voltage region and a first grounded region surrounding the first high voltage region;
a second high voltage electrode, comprising a second high voltage region and a second grounded region surrounding the second high voltage region;
a dual-sided segmented electrode, disposed between the first high voltage electrode and the second high voltage electrode, comprising a first detection region disposed correspondingly to the first high voltage region, a second detection region having a rear side facing the first detection region and disposed correspondingly to the second high voltage region, a third grounded region surrounding the first detection region and the second detection region, a first reading electrode disposed in the first detection region, and a second reading electrode disposed in the second detection region;

a first spacing member, disposed between the first high voltage electrode and the dual-sided segmented electrode, comprising a first frame body connected to the first grounded region and the third grounded region, and a first ionization cavity formed by the first frame body surrounding the first high voltage region and the first detection region, the first reading electrode being accommodated in the first ionization cavity; and a second spacing member, disposed between the second high voltage electrode and the dual-sided segmented electrode, comprising a second frame body connected to the second grounded region and the third grounded region, and a second ionization cavity formed by the second frame body surrounding the second high voltage region and the second detection region, the second reading electrode being accommodated in the second ionization cavity.

2. The detector for measuring scanning ion beams in radiation therapy of claim 1, wherein the first spacing member and the second spacing member have a thickness of 3 mm.

3. The detector for measuring scanning ion beams in radiation therapy of claim 1, wherein the first reading electrode comprises a plurality of longitudinal electrodes, and the second reading electrode comprises a plurality of lateral electrodes.

4. The detector for measuring scanning ion beams in radiation therapy of claim 3, wherein the longitudinal electrodes are spaced by 2 mm from one another.

5. The detector for measuring scanning ion beams in radiation therapy of claim 3, wherein the lateral electrodes are spaced by 2 mm from one another.

6. The detector for measuring scanning ion beams in radiation therapy of claim 1, wherein the first spacing member further comprises a first ventilation portion disposed at the first frame body, the second spacing member further comprises a second ventilation portion disposed at the second frame body, and the first ionization cavity and the second ionization cavity are in communication with an exterior via the first ventilation portion and the second ventilation portion.

7. The detector for measuring scanning ion beams in radiation therapy of claim 1, further comprising a first fastening member and a second fastening member, the first fastening member disposed at one side of the first high voltage electrode away from the dual-sided segmented electrode, the second fastening member disposed at one side of the second high voltage electrode away from the dual-sided segmented electrode.

8. A detector for measuring scanning ion beams in radiation therapy, comprising:

a first high voltage electrode, comprising a first high voltage region, and a first grounded region surrounding the first high voltage region;

a segmented electrode assembly, disposed at one side of the first high voltage electrode, comprising:

a segmented electrode, comprising a plurality of first reading electrodes and a plurality of second reading electrodes, the first reading electrodes and the second reading electrodes extending along different directions, respectively;

a substrate, carrying the segmented electrode, comprising an upper substrate, a lower substrate, and an intermediate layer disposed between the upper substrate and the lower substrate; the upper substrate comprising an upper surface, a plurality of first through holes penetrating the upper surface and being in communication with the first reading electrodes, and a plurality of second through holes penetrating the upper surface and being in communication with the second reading electrodes; the upper surface comprising a first detection region disposed correspondingly to the first high voltage region, and a third grounded region surrounding the first detection region; and an inner connecting line, comprising a plurality of first conductive sections disposed at the first through holes and electrically connected to the first reading electrodes, a plurality of first conductive wires disposed on the lower substrate and electrically connected to the first conductive sections, a plurality of second conductive sections disposed at the second through holes and electrically connected to the second reading electrodes, and a plurality of second conductive wires disposed on the intermediate layer and electrically connected to the second conductive sections; and a first spacing member, disposed between the first high voltage electrode and the segmented electrode assembly, comprising a first frame body connected to the first grounded region and the third grounded region, and a first ionization cavity formed by the first frame body surrounding the first high voltage region and the first detection region.

9. The detector for measuring scanning ion beams in radiation therapy of claim 8, wherein a thickness of the first spacing member is 3 mm.

10. The detector for measuring scanning ion beams in radiation therapy of claim 8, wherein the first reading electrodes are spaced by 2 mm from one another.

11. The detector for measuring scanning ion beams in radiation therapy of claim 8, wherein the second reading electrodes are spaced by 2 mm from one another.

12. The detector for measuring scanning ion beams in radiation therapy of claim 8, wherein the first spacing member further comprises a first ventilation portion disposed at the first frame body, and the first ionization cavity is in communication with an exterior via the first ventilation portion.

13. The detector for measuring scanning ion beams in radiation therapy of claim 8, further comprising a first fastening member disposed at one side of the first high voltage electrode away from the segmented electrode assembly.

* * * * *